US00PP16793P2

(12) United States Plant Patent
May et al.

(10) Patent No.: US PP16,793 P2
(45) Date of Patent: Jul. 11, 2006

(54) ***CHRYSANTHEMUM* PLANT NAMED 'JMAY03'**

(50) Latin Name: *Chrysanthemum morifolium*
Varietal Denomination: JMAY03

(75) Inventors: James May, San Luis Obispo, CA (US); Gerardo Martinez, San Luis Obispo, CA (US)

(73) Assignee: May Greenhouses, Inc., San Luis Obispo, CA (US)

( * ) Notice: Subject to any disclaimer, the term of this patent is extended or adjusted under 35 U.S.C. 154(b) by 32 days.

(21) Appl. No.: 11/038,747

(22) Filed: Jan. 18, 2005

(51) Int. Cl.
*A01H 5/00* (2006.01)

(52) U.S. Cl. ..... Plt./295
(58) Field of Classification Search ..... Plt./295
See application file for complete search history.

*Primary Examiner*—Anne Marie Grunberg
*Assistant Examiner*—Annette H Para
(74) *Attorney, Agent, or Firm*—Knobbe Martens Olson & Bear, LLP

(57) ABSTRACT

A new and distinct *Chrysanthemum* plant cultivar is disclosed, characterized by having large daisy-form flowers with golden yellow ray florets and very good floral longevity. The plant has strong stems and a strong, spreading growth habit and slightly sparse foliage.

2 Drawing Sheets

Latin name of the genus and species: *Chrysanthemum morifolium.*
Variety denomination: 'JMAY03'.

BACKGROUND OF THE INVENTION

The new cultivar 'JMAY03' is a discovered natural mutation of the parent *Chrysanthemum* plant variety 'Pelee'. The new cultivar was discovered in a cultivated state by James May and Gerardo Martinez in San Luis Obispo, Calif., during the month of September, 2002, and selected by Gerardo Martinez in San Luis Obispo, Calif., during the month of January, 2003.

Asexual reproduction of the new cultivar 'JMAY03' was first performed by Gerardo Martinez in October, 2002. The asexual reproduction was performed by terminal cuttings in a controlled environment (greenhouse) in San Luis Obispo, Calif., and has shown that the unique features of this cultivar are stable and reproduced true to type on successive generations.

SUMMARY OF THE INVENTION

The cultivar 'JMAY03' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'JMAY03'. These characteristics in combination distinguish 'JMAY03' as a new and distinct *Chrysanthemum* cultivar:

1. The flower has golden yellow ray florets.
2. The flower is a large (10–12 cm) daisy flower form.
3. The plant has a strong spreading growth habit with slightly sparse foliage.
4. The branches have about four to six breaks per stem on a single pinch.
5. The plant has very good floral longevity.
6. The flowers hold color well with maturity.

7. The plant vigor is excellent.
8. The plant has strong stems.

Plants of the new cultivar 'JMAY03' are similar to plants of the parent variety, 'Pelee' (U.S. Plant Pat. No. 8,464) in most horticultural characteristics, including floral form, growth habit, and plant vigor, but is distinguished from 'Pelee' by its pure golden yellow ray florets. Additionally, the ray florets of the new cultivar 'JMAY03' hold their color as they mature better than the ray florets of 'Pelee'.

In comparison to the commercially available variety 'Miramar' (U.S. Plant Pat. No. 7,469), the new cultivar 'JMAY03' has a larger, golden yellow flower with broader and more expansive ray florets. Further, plants of the new variety have a faster response time and have more open growth with lighter foliage color than the comparable variety. The new variety has a longer post-production shelf life than the comparable variety 'Miramar.' Further, the new variety has slightly more vigorous growth than the comparable variety.

BRIEF DESCRIPTION OF THE PHOTOGRAPHS

Figure 1:
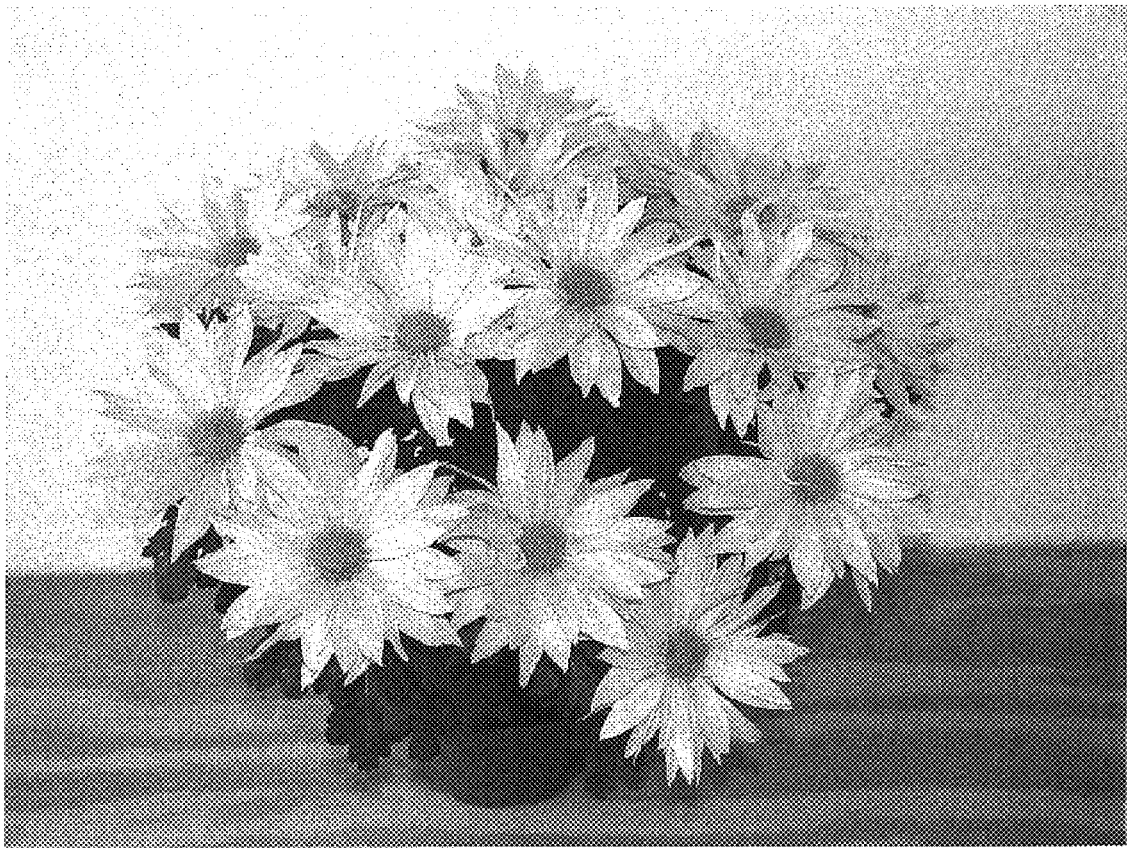
Figure 2:
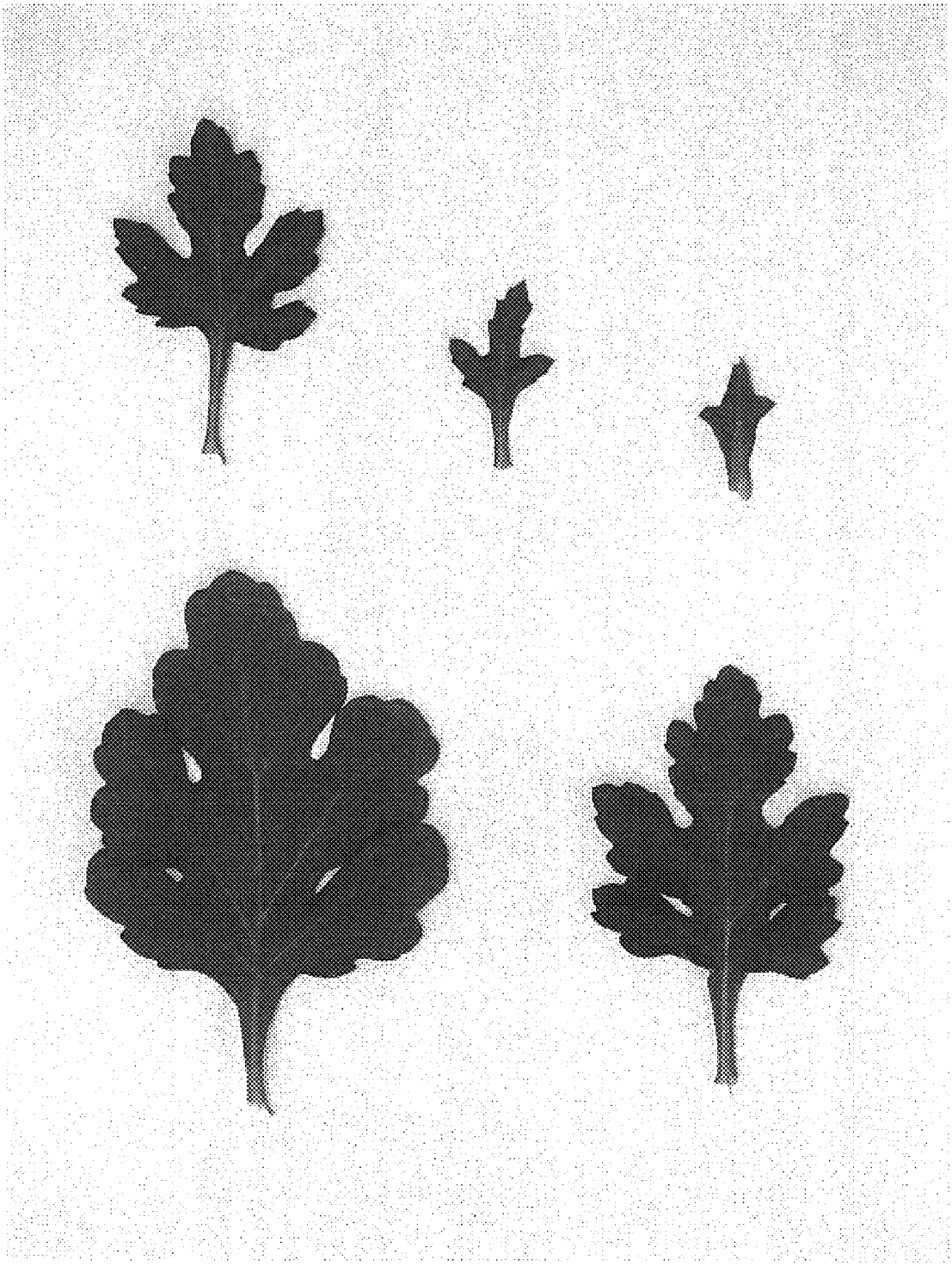

The accompying photograph in FIG. 1 illustrates in full color a typical plant of 'JMAY03' which was grown in a greenhouse. The plant was photographed eight weeks after the start of the short-day treatment. The 6.5" container held five cuttings. FIG. 2 is a photograph of several leaves from the 'JMAY03' plant. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'JMAY03' that are 10 weeks old from terminal cuttings. The plants were grown in a greenhouse with bright and sunny light conditions in San Luis Obispo, Calif., during the month of August 2004. The growing temperature ranged from 65° F. to 70° F. at night to 75° F. to 80° F. during the day. Measurements and numerical values represent averages of typical flowering types, and are believed to apply to plants of the variety grown under similar conditions of soil and climate elsewhere:

Commercial classification: Florist-type *Chrysanthemum.*

PROPAGATION

Time to rooting: Approximately 10 to 14 days at 72° C.
Root description: Vigorous and well-branched.
Root texture: Fibrous.

PLANT

Plant type: Herbaceous perennial.
Growth habit: Semi-upright.
Height: Approximately 25–35 cm as a disbud pot mum with 0–7 long days after pinch.
Plant spread: Approximately 40–45 cm.
Growth rate: Approximately 3–4 cm per week after pinch.
Branching characteristics: Alternate.
Stem characteristics:
*Lateral branch length.*—Approximately 20–25 cm.
*Lateral branch diameter.*—Approximately 4–6 mm.
*Internode length.*—Approximately 1 cm to 5 cm.
*Stem color.*—Near Green 138C.
*Stem and stem base strength.*—Very strong.
*Texture.*—Pubescent.
*Habit.*—Ascending.

FOLIAGE

Leaf:
*Arrangement.*—Alternate.
*Leaf type.*—Simple.
*Number of leaves per lateral branch.*—Approximately 12–15.
*Juvenile leaf — width.*—Approximately 10–15 mm.
*Juvenile leaf — length (exluding petiole).*—Approximately 15–25 mm.
*Mature leaf — width.*—Approximately 50–70 mm.
*Mature left — length (excluding petiole).*—Approximately 60–80 mm.
*Shape of blade.*—Lanceolate to obovate (moderately to deeply lobed and slightly serrate).
*Apex.*—Acute (slightly serrate).
*Base.*—Attenuate.
*Attachment.*—Attenuate to stem.
*Margin.*—Moderately to deeply lobed and slightly serrate.
*Aspect.*—Juvenile leaves slightly cupped, changing at times to slightly recurved in mature foliage.
*Texture of top surface.*—Canescent.
*Texture of bottom surface.*—Pubescent.
*Color.*—Young foliage upper side: Near Green 139A. Young foliage under side: Near Green 138A. Mature foliage upper side: Near Green 141A. Mature foliage under side: Near Green 138B.
*Venation.*—Venation color upper side: Near Green 138C. Venation color under side: Near Green 139D. Venation type: Palmately compound.
Petiole: None (leaf is attenuate to stem).
Stipules:
*Number per leaf.*—2.
*Color.*—Near Green 141A.
*Length.*—Approximately 10 mm.
*Width.*—Approximately 8 mm.
*Shape.*—Deltoid.

BLOOM

Flowering stem:
*Length.*—At terminal end (shortest): Approximately 1 cm. At lateral end (longest): Approximately 4 cm.
*Angle to stem.*—Approximately 10–30 degrees.
*Strength.*—Strong.
*Color.*—Near Green 138D.
*Habit.*—Erect.
*Diameter.*—Approximately 3–5 mm.
*Surface texture.*—Pubescent.
Flower bud:
*Length.*—Approximately 8–10 mm.
*Diameter.*—Approximately 12–14 mm.
*Form.*—Globular.
*Color.*—Near Green 143B.
*Rate of flower opening.*—Approximately 14–21 days.
Involucral bracts (phyllaries):
*Appearance.*—Matte.
*Texture.*—Pubescent.
*Number per flower.*—Approximately 30–50.
*Shape.*—Ovate.
*Margin.*—Entire.
*Apex.*—Acute.
*Length.*—Approximately 8–10 mm.
*Width.*—Approximately 2–4 mm.
*Color.*—Upper side: Near Green 143A. Under side: Near Green 143A.
Flower:
*Flowering habit.*—Twelve hours of darkness per day for 52–58 days required to develop blooms.
*Flower form.*—Flat capitulum type daisy.
*Natural flowering season.*—Fall.
*Number of flowers per lateral branch.*—Approximately 6–8.
*Flower diameter.*—Approximately 10–12 cm.
*Flower depth.*—Approximately 2–3 cm.
*Flower longevity on plant.*—Approximately 21 to 28 days.
*Persistence.*—Persistant.
*Receptacle shape.*—Rotund-dome like.
*Disc diameter.*—Approximately 2–2.5 cm.
*Changes as the flower ages.*—The flower opens with a golden yellow color and fades only slightly as it matures. The nearly vertical ray florets begin to reflex and move towards horizontal as the flower matures. The disc florets mature exposing stigmas from outer edge of disc towards the center.
Ray florets:
*Appearance.*—Matte.
*Arrangement.*—Rosette.
*Texture.*—Smooth to satiny.
*Average number per flower.*—Approximately 30.
*Shape.*—Oblanceolate.
*Aspect.*—Recurving.
*Cross section.*—Concave.
*Margin.*—Entire.
*Apex.*—Acute.
*Strength.*—Strong.
*Length.*—Approximately 6 cm.
*Width.*—Approximately 2 cm.
*Length of corolla tube.*—Approximately 2–3 mm.
*Color.*—Upper surface at first opening: Near Yellow 9A. Upper surface at maturity: Near Yellow 9A.

Upper surface at fading: Near Yellow 9B. Under surface at first opening: Near Yellow 7C. Under surface at maturity: Near Yellow 7D. Under surface at fading: Near Yellow 7D.

Disc florets:

*Appearance.*—Matte.
*Texture.*—Waxy.
*Average number of florets per disc.*—Approximately 200–250.
*Shape.*—Rounded.
*Apex.*—Syngenesious.
*Average length.*—Approximately 4–5 mm.
*Average width.*—Approximately 1 mm.
*Color.*—At first opening: Near Yellow-green 151B. At maturity: Near Yellow-orange 14B. At fading: Near Yellow-green 153D.

REPRODUCTIVE ORGANS

Ray florets:

*Number of pistils per floret.*—1.
*Stigma shape.*—2-Branched.
*Stigma color.*—Near Yellow 13B.
*Style color.*—Near Green-yellow 1C.
*Style length.*—Approximately 6–7 mm.
*Stamens.*—Absent.

Disc Florets:

*Number of pistils per floret.*—1.
*Stigma shape.*—2-branched.
*Stigma color.*—Near Yellow 7A.
*Style length.*—Approximately 5 mm.
*Style color.*—Near Green-yellow 1A.
*Number of stamens per floret.*—5.
*Anther shape.*—Syngenesious.
*Anther color.*—Near Yellow 7A.
*Pollen color.*—Near Yellow 7A.
*Pollen quantity.*—Low.

OTHER CHARACTERISTICS

Seed production: Seeds are not produced in this variety.

Disease resistance: Very good to excellent resistance to most common *chrysanthemum* diseases.

Pest resistance: The plant is susceptible to most common greenhouse pests.

Drought tolerance and cold tolerance: This variety is not drought or cold tolerant.

What is claimed is:

1. A new and distinct cultivar of *Chrysanthemum* plant as herein illustrated and described.

* * * * *

UNITED STATES PATENT AND TRADEMARK OFFICE

CERTIFICATE OF CORRECTION

PATENT NO. : PP 16,793 P2
APPLICATION NO. : 11/038747
DATED : July 11, 2006
INVENTOR(S) : James May and Gerardo Martinez It is certified that error appears in the above-identified patent and that said Letters Patent is hereby corrected as shown below:

Column 2, line 23, delete “accompying” and insert --accompanying-- therefor.

Column 2, line 33 (approx.), delete “The” and insert --the-- therefor.

Column 3, line 32, delete “(exluding” and insert --(excluding-- therefor.

Column 3, line 35, delete “left” and insert --leaf-- therefor.

Signed and Sealed this

Nineteenth Day of December, 2006

JON W. DUDAS
*Director of the United States Patent and Trademark Office*